US010791981B2

United States Patent
Srinivasan

(10) Patent No.: US 10,791,981 B2
(45) Date of Patent: Oct. 6, 2020

(54) NEURO ATTACK PREVENTION SYSTEM, METHOD, AND APPARATUS

(71) Applicant: S Square Detect Medical Devices, Andover, MA (US)

(72) Inventor: Govindarajan T. Srinivasan, Andover, MA (US)

(73) Assignee: S SQUARE DETECT MEDICAL DEVICES, Andover, MA (US)

( * ) Notice: Subject to any disclaimer, the term of this patent is extended or adjusted under 35 U.S.C. 154(b) by 262 days.

(21) Appl. No.: 15/614,614

(22) Filed: Jun. 6, 2017

(65) Prior Publication Data

US 2017/0347937 A1    Dec. 7, 2017

Related U.S. Application Data

(60) Provisional application No. 62/346,172, filed on Jun. 6, 2016.

(51) Int. Cl.
*A61B 5/00* (2006.01)
*A61B 5/026* (2006.01)
(Continued)

(52) U.S. Cl.
CPC .......... *A61B 5/4076* (2013.01); *A61B 5/0075* (2013.01); *A61B 5/0261* (2013.01);
(Continued)

(58) Field of Classification Search
CPC ....... A61B 5/0075; A61B 5/0261; A61B 5/40; A61B 5/4064; A61B 5/4076;
(Continued)

(56) References Cited

U.S. PATENT DOCUMENTS 5,095,517 A * 3/1992 Monguzzi ................ G02B 6/32
                                                          250/227.11
5,706,821 A   1/1998 Matcher et al.
(Continued)

FOREIGN PATENT DOCUMENTS

WO        2014099124 A1   6/2014
WO    WO-2015092872 A1 * 6/2015 ........... A61B 5/7214
(Continued)

OTHER PUBLICATIONS

Kety, S. S., & Schmidt, C. F. (1948). The effects of altered arterial tensions of carbon dioxide and oxygen on cerebral blood flow and cerebral oxygen consumption of normal young men. The Journal of clinical investigation, 27(4), 484-492. (Year: 1948).*
(Continued)

*Primary Examiner* — Devin B Henson
(74) *Attorney, Agent, or Firm* — Nelson Mullins Riley & Scarborough LLP; Thomas J. Engellenner; Reza Mollaaghababa

(57) ABSTRACT

A portable biomedical device for detecting ischemic stroke in the brain is provided. The device provides portability and compactness and can accommodate software for resolving blood flow velocity measurements. The device can provide both a diagnostic and a predictive tool for determining the occurrence of an ischemic attack, one such example being transient ischemic attack (TIA) not only at hospital bedside but also in a home environment.

14 Claims, 5 Drawing Sheets

(51) Int. Cl.
  G16H 50/20 (2018.01)
  A61B 5/02 (2006.01)
  A61B 5/022 (2006.01)
  A61B 5/04 (2006.01)
  G06F 3/01 (2006.01)
  A61B 5/08 (2006.01)
  G16H 40/67 (2018.01)
  A61B 5/0205 (2006.01)
  A61B 5/145 (2006.01)

(52) U.S. Cl.
  CPC ........ A61B 5/04004 (2013.01); A61B 5/0816 (2013.01); A61B 5/4064 (2013.01); A61B 5/6814 (2013.01); A61B 5/7275 (2013.01); G06F 3/015 (2013.01); G16H 40/67 (2018.01); G16H 50/20 (2018.01); A61B 5/022 (2013.01); A61B 5/0205 (2013.01); A61B 5/02028 (2013.01); A61B 5/02055 (2013.01); A61B 5/14542 (2013.01); A61B 5/6803 (2013.01); A61B 5/7264 (2013.01); A61B 2505/07 (2013.01); A61B 2562/0233 (2013.01)

(58) Field of Classification Search
  CPC ................ A61B 5/6803; A61B 5/6814; A61B 2562/0233; A61B 5/04004; A61B 5/7275; A61B 5/02028; A61B 5/0205; A61B 5/022
  See application file for complete search history.

(56) References Cited

U.S. PATENT DOCUMENTS

| | | | | |
|---|---|---|---|---|
| 6,223,069 | B1* | 4/2001 | Pfeiffer | A61B 5/0261 600/310 |
| 6,802,812 | B1* | 10/2004 | Walker | A61B 5/02028 600/309 |
| 6,944,487 | B2 | 9/2005 | Maynard et al. | |
| 9,538,949 | B2 | 1/2017 | Al-Ali et al. | |
| 9,867,548 | B2* | 1/2018 | Le | A61B 5/04 |
| 10,076,279 | B2* | 9/2018 | Nahum | A61B 5/11 |
| 2007/0287922 | A1* | 12/2007 | Tanaka | A61B 5/0261 600/485 |
| 2008/0259337 | A1* | 10/2008 | Sagara | A61B 5/0261 356/432 |
| 2008/0275352 | A1* | 11/2008 | Shapira | A61B 5/0261 600/506 |
| 2009/0270745 | A1* | 10/2009 | Sankai | A61B 5/0261 600/504 |
| 2009/0281403 | A1* | 11/2009 | Benni | A61B 5/14553 600/331 |
| 2012/0238883 | A1* | 9/2012 | Inoue | A61B 5/0059 600/476 |
| 2013/0150726 | A1* | 6/2013 | Riley | A61B 5/0059 600/473 |
| 2014/0073888 | A1* | 3/2014 | Sethi | A61B 5/021 600/324 |
| 2014/0107494 | A1* | 4/2014 | Kato | A61B 5/7267 600/473 |
| 2015/0031980 | A1* | 1/2015 | Yun | A61B 5/4064 600/410 |
| 2015/0038811 | A1* | 2/2015 | Asaka | A61B 5/0042 600/324 |
| 2015/0038812 | A1 | 2/2015 | Ayaz et al. | |
| 2015/0105672 | A1* | 4/2015 | Ishikawa | A61B 5/14553 600/479 |
| 2015/0223694 | A1* | 8/2015 | Funane | A61B 5/1455 600/407 |
| 2015/0297124 | A1* | 10/2015 | Ishikawa | A61B 5/0042 600/328 |
| 2015/0366514 | A1* | 12/2015 | Fantini | A61B 5/0075 600/301 |
| 2016/0015316 | A1* | 1/2016 | Borsook | A61B 5/0075 600/340 |
| 2016/0345880 | A1* | 12/2016 | Nakaji | A61B 5/0261 |
| 2017/0105671 | A1* | 4/2017 | Borgos | A61B 5/02028 |
| 2017/0172479 | A1* | 6/2017 | Hirshfield | A61B 5/14553 |
| 2017/0281014 | A1* | 10/2017 | von Luehmann | A61B 5/4064 |
| 2017/0311803 | A1* | 11/2017 | Hirsch | A61B 5/4836 |
| 2017/0340260 | A1* | 11/2017 | Chowdhury | A61N 1/20 |
| 2018/0070831 | A1* | 3/2018 | Sutin | A61B 5/6814 |

FOREIGN PATENT DOCUMENTS

| | | | | |
|---|---|---|---|---|
| WO | WO-2015177876 | A1* | 11/2015 | ......... A61B 5/0082 |
| WO | WO-2016103323 | A1* | 6/2016 | ......... A61B 5/14552 |

OTHER PUBLICATIONS

Kety, S. S., & Schmidt, C. F. (1948). The nitrous oxide method for the quantitative determination of cerebral blood flow in man: theory, procedure and normal values. The Journal of clinical investigation, 27(4), 476-483. (Year: 1948).*

Newell, D. W., Aaslid, R., Lam, A., Mayberg, T. S., & Winn, H. R. (1994). Comparison of flow and velocity during dynamic autoregulation testing in humans. Stroke, 25(4), 793-797. (Year: 1994).*

Ali, A. M., Green, D., Zayed, H., Halawa, M., El-Sakka, K., & Rashid, H. I. (2011). Cerebral monitoring in patients undergoing carotid endarterectomy using a triple assessment technique. Interactive cardiovascular and thoracic surgery, 12(3), 454-457. (Year: 2011).*

Pellicer, A., & del Carmen Bravo, M. (Feb. 2011). Near-infrared spectroscopy: a methodology-focused review. In Seminars in fetal and neonatal medicine (vol. 16, No. 1, pp. 42-49). WB Saunders. (Year: 2011).*

Scholkmann, F., Kleiser, S., Metz, A. J., Zimmermann, R., Pavia, J. M., Wolf, U., & Wolf, M. (2014). A review on continuous wave functional near-infrared spectroscopy and imaging instrumentation and methodology. Neuroimage, 85, 6-27. (Year: 2014).*

Newell, D. W., Aaslid, R., Lam, A., Mayberg, T. S., & Winn, H. R. (1994). Comparison of flow and velocity during dynamic autoregulation testing in humans. Stroke, 25(4), 793-797. (Year: 1994).*

Ali, A. M., Green, D., Zayed, H., Halawa, M., El-Sakka, K., & Rashid, H. I. (2011). Cerebral monitoring in patients undergoing carotid endarterectomy using a triple assessment technique. Interactive cardiovascular and thoracic surgery, 12(3), 454-457. (Year: 2011).*

Kainerstorfer, J. M., Sassaroli, A., & Fantini, S. (2014). Coherent hemodynamics spectroscopy in a single step. Biomedical optics express, 5(10), 3403-3416. (Year: 2014).*

* cited by examiner

NEURO ATTACK PREVENTION SYSTEM, METHOD, AND APPARATUS

RELATED APPLICATIONS

The subject matter of this application is related to U.S. Provisional Application No. 62/346,172, filed on Jun. 6, 2016, which application is incorporated herein by reference.

BACKGROUND

The present invention relates to systems, methods and biomedical devices for neuro attack prevention, and more particularly to detection of transient ischemic attack (TIA) events.

The medical community considers TIA as a precursor or warning indicator for an impending and disabling ischemic stroke. According to World Health Organization (WHO), stroke is the 2nd largest killer worldwide impacting over 15 million people. In the US alone, stroke has affected over 7 million Americans, causing over 150,000 deaths every year. Annually, over 500,000 patients suffer from TIA and less than 40% of them seek medical help. This is primarily due to the fact that typical TIA symptoms last for less than 15 minutes and the patient feels completely normal after that, providing false reassurance. However, approximately 15% of all TIA patients will have an ischemic stroke within 3 months. Over 2% of US population lives with permanent long-term disability from stroke that is preventable, causing an economic burden of over $70 billion (2015) annually. Existing techniques for diagnosing TIA are inaccurate, inefficient, subjective, and expensive.

Magnetic Resonance Imaging (MRI) measurements are limited by availability in the acute setting as it is not the standard-of-care in the emergency room (ER) setting. Furthermore, the associated high cost-per-scan in combination with its non-portability restricts its use as an affordable or portable diagnostic tool. Unlike MRI, transcranial Doppler (TCD) allows for direct measurements of blood flow velocity but not tissue state (ischemia vs. infarction). Its capability for monitoring the blood flow velocity is also limited by the ultrasound beam penetration that depends on the patient temporal bone anatomy, thus limiting its application in all patients. Moreover, the blood flow velocity measurements provided by TCD reflect macro-vascular changes, thus reducing its specificity as a valid diagnostic tool for small vessel or branch vessel occlusions causing ischemic stroke or TIA. Another tool, EEG, is a portable and relatively inexpensive technology that relies on neural electrical signals. However, its ability to directly measure cerebral hemodynamics has not been established.

Limitations in Current Technologies: Diagnostic assessment for ischemic stroke and TIA diagnosis are mainly dominated by magnetic resonance imaging (MRI) with diffusion weighted imaging and perfusion weighted imaging. These imaging techniques are costly, are predominately located at fixed medical facilities, and often require scheduling well in advance.

As can be seen, there is a need for TIA detection capability that is portable and compact diagnostic and predictive tool for ischemic attack such as TIA; not only at hospital bedside but also in a home environment.

Patents to refer include: U.S. Pat. Nos. 5,706,821, 6,944,487, 9,538,949, Pub No: US 2015/0038812 A1, Pub No: WO2014099124 A1.

SUMMARY

Embodiments provide a system, method and biomedical apparatus for detecting ischemic stroke in the brain.

DETAILED DESCRIPTION

In the following description, references are made to various embodiments in accordance with which the disclosed subject matter can be practiced. Multiple references to "one embodiment" or "an embodiment" do not necessarily refer to the same embodiment. Particular features, structures or characteristics associated with such embodiments can be combined in any suitable manner in various embodiments. References are also made to the accompanying drawings in which the same reference numbers are used throughout to refer to the same or like components.

A Neuro Attack Prevention (NAP) device of the present invention is designed for early detection of acute ischemic stroke and, in particular, incidents of transient ischemic attack (TIA), also known as reversible or mini-stroke. The unique capabilities of the NAP device enable portability and compactness. In addition the system and method are able to accommodate software that can resolve blood flow velocity measurements, enable us to leverage multi-modality system benefits while using simple single modality instrumentation. This unique value proposition makes this hardware device an ideal diagnostic and predictive tool for ischemic attack such as TIA; not only at hospital bedside but also in a home environment.

The NAP device provides a portable non-invasive diagnostic device that will significantly improve diagnosis of acute brain infarction with the potential for earlier evaluation and interventions for patients with acute ischemic stroke and TIA. The NAP scanning device of the present invention provides a low-cost, compact, portable device that provides an enhanced diagnosis compared to clinical assessments using the FAST (Face, Arms, Speech and Time) protocol that is prevalent today both at home and at ambulatory care centers (emergency rooms, outpatient clinics) and ABCD2 risk scoring tool (ABCD2 score is based on five parameters such as age, blood pressure, clinical features, duration of TIA, and presence of diabetes) that is the primary clinical prediction rule used today to detect TIA in ER and clinics.

The Neuro Attack Prevention (NAP) device will also significantly enhance diagnosis of cerebrovascular ischemic events at the bedside and also enable pre-hospital diagnosis of acute stroke prior to having a CT or an MRI completed. This will save precious time in the pre-admission management of TIA events, possibly allowing for appropriate routing of patients to stroke centers and earlier intervention to improve outcomes. Furthermore, it may be utilized in hospital and outpatient settings for the detection of recurrent ischemic events after an initial TIA event.

Figure 1:
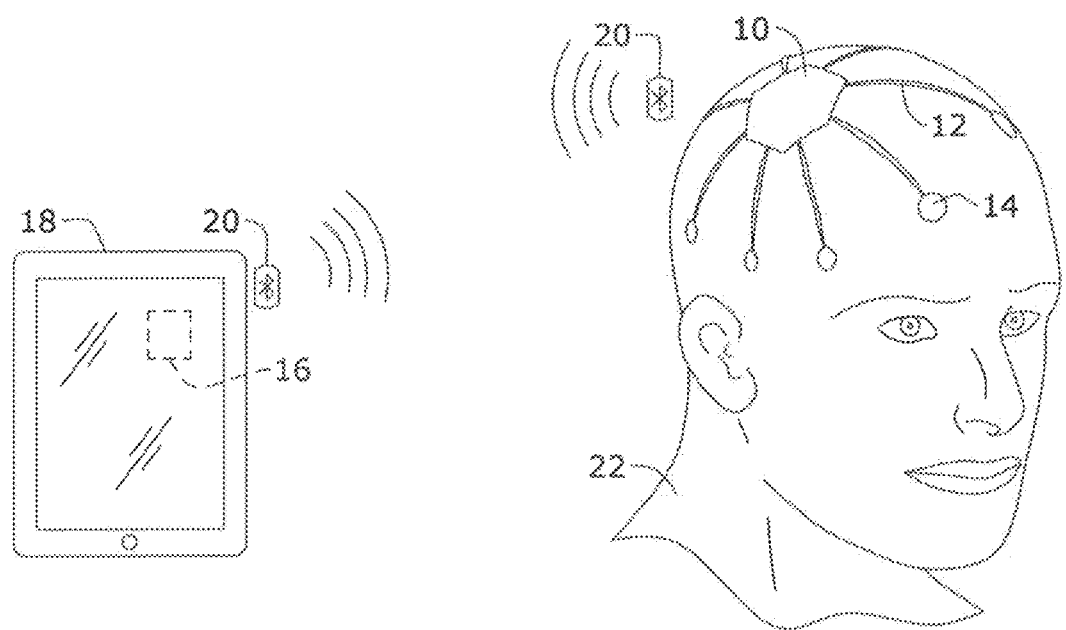
FIG. 1 shows a Neuro Attack Prevention NAP device placed on a human head.

An embodiment of the NAP device contemplated by the present invention is shown in reference to FIG. 1. FIG. 1 is a perspective invention shown in use. FIG. 1 shows the NAP device placed on a human head (predominantly on one side) for illustrations; the device can be placed in the center of the head as well. [10] is the hub; [12] are the spokes ; [14] is the light emitting sources and detector couplings; [16] is the software ; [18] is the tablet or phone device; [20] are the Bluetooth hardware and communication between NAP device and commercial tablet/phone; and [22] is the user.

Figure 2:
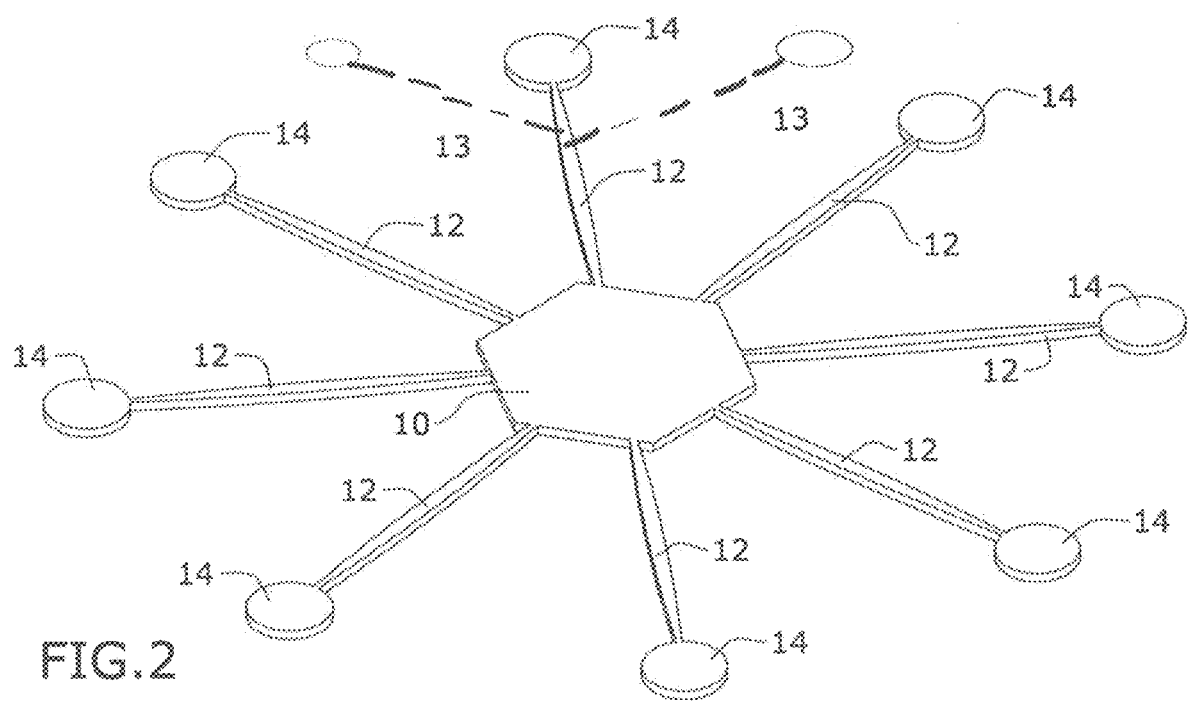
FIG. 2 is the perspective view of the invention or the device shown in standalone mode.

The overall device consists of a plurality of spokes emanating from a centralized hub as shown in FIG. 2. FIG. 2 is the perspective view of the invention or the device shown in standalone mode. [10] is the hub; [12] are the spokes; [13] is the hinge design that can swivel left and right (currently shown only in 1 spoke); and [14] is the light emitting sources and detector couplings.

Each such spokes includes a pair of light emitting sources and a photo-diode based detector, each placed at a specified distance varying from 2.5-3.5 cm. The source may be a LED or laser device. Each source can be fired either simultaneously or in sequence. The respective detector positioned in the appropriate spoke reads each source signal.

Each spoke, with its associated source-detector, targets a specified region of the brain, such as 2 on the frontal lobe, 1 for right side temporal lobe, 1 for left side temporal lobe, 1 for right side of area close to the cerebellum, 1 for left side of area close to the cerebellum, 1 for the occipital lobe and 1 for the parietal lobe. Each spoke can be split in the middle with a hinge; the hinge supports an extension with sources on one and the detector on the other.

The hub houses the data acquisition electronics and the communication hardware and software protocols such as Bluetooth or wireless. Note: for illustrative purposes, only one side of the brain is shown in FIG. 1. The multi-array sensor is placed on the patient head, will provide an extensive source-detector grid to allow for a comprehensive hemodynamic assessment of the subject's brain.

Preferably, there will be at least 8 probes in total. Each probe will have a source-detector pair. The source-detector separation distance will be on the order of about 3 cm. The sources wavelength will be modulated to 690 nm and 830 nm. The same detector may be used to capture the light emitted by the sources at the two varying wavelengths, separated by time. The modulating frequency should preferably be >3 Hz, consistent with the frequency spectrum of the spontaneous hemodynamic oscillations in the brain where the highest component is due to arterial pulsation (~1-1.5 Hz).

A unique feature of the NAP device is its ability to discern depth information, this can be made available by performing multi-distance measurements using a plurality of sources disposed at different distances on the spoke that are laced on the same probe and configured to share the same detector. This approach will facilitate the data analysis procedure by removing the more superficial hemodynamics contributions, thus leaving with cerebral hemodynamic oscillations.

At least two pneumatic cuffs and a heart rate monitor will be wrapped around the subject's upper arms. After a 5-10 minute baseline collection, the cuffs will be inflated to a pressure of 180-200 mmHg, which is above systolic blood pressure, kept inflated for 2.5 minutes, and then suddenly released. This procedure induced a systemic drop (by 10-25 mmHg) in mean arterial pressure and recovery to baseline within approximately 25 seconds. After 5 minutes of recovery, the two upper arm cuffs will be cyclically inflated (to 200 mmHg) and deflated at five frequencies in the range 0.03-0.12 Hz for a time of 2-3 min per each frequency (12 min total). A final 5 min period of recovery data collection will follow. This protocol lasts less than 30 minutes and provides dynamic NIRS data that can be analyzed with Coherent Hemodynamic Spectroscopy CHS methods. The heart rate of the subject will be monitored and kept within a maximum of 130-150 beats per minute throughout the entire procedure.

In another embodiment, the Neuro Attack Prevention NAP system can be envisioned to use a gas mask and a respiratory rate monitor instead of a cuff, the mask would inject controlled carbon dioxide ($CO_2$) which is inhaled by the subject and this causes the perturbations in the blood flow, both cerebral blood flow and cerebral blood volume, in the brain. The NAP device synchronizes the data collection to the $CO_2$ ingestion of the subject, which creates the same temporal or time varying perturbations as the cuff. The respiratory rate of the subject will be monitored and kept within acceptable ranges of $CO_2$ levels throughout the entire procedure.

Figure 3:
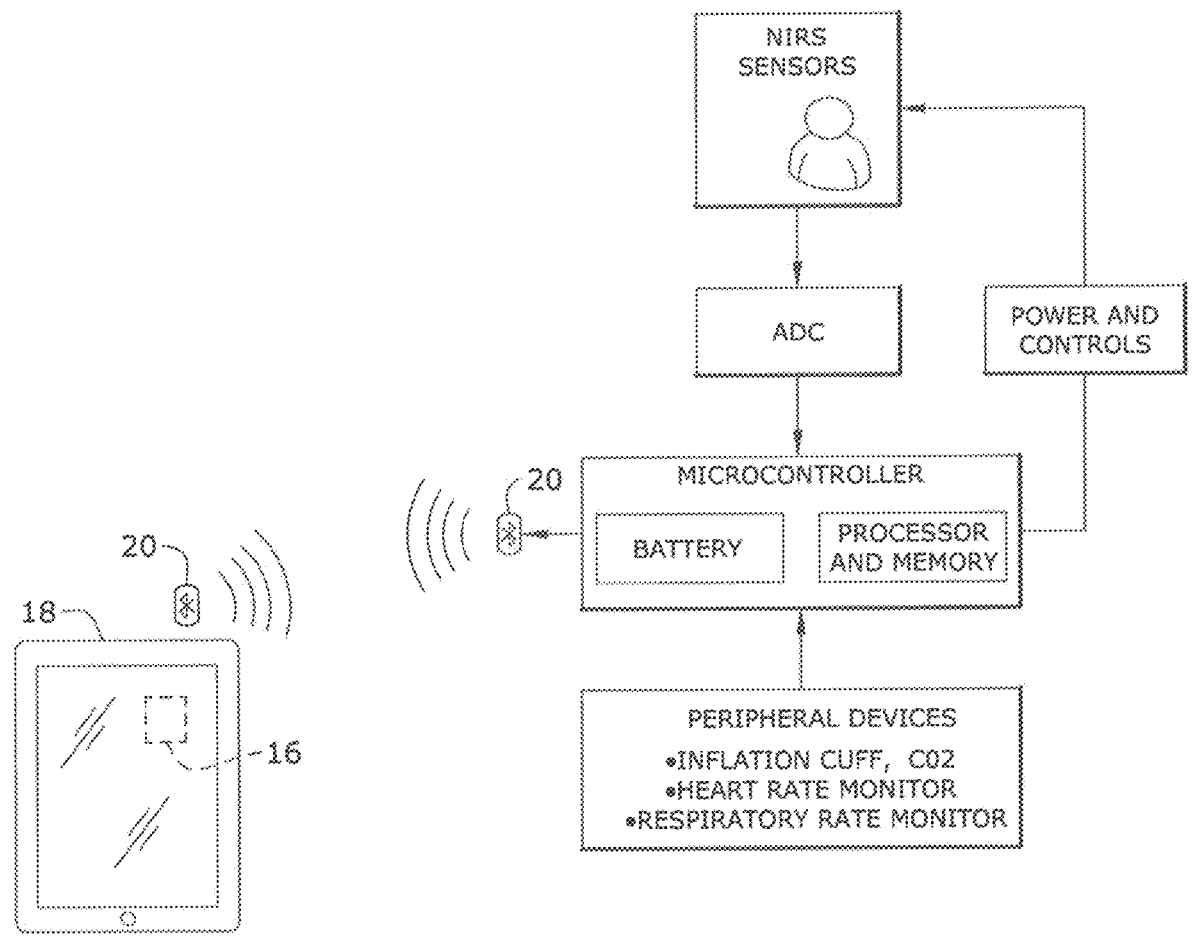
FIG. 3 shows the block diagram of the hardware solution, the avalanche photodiode APD signal is digitized in a high speed analog-to-digital converter ADC.

A software control mechanism on the NAP device, shown in is used to in conjunction with the data acquisition electronics to fire the light sources at different wavelength and to capture and collect the detector data aligned with the phase of the compression of the cuff expansion and contraction. FIG. 3 is a schematic of the invention along with the functional sequence of the NAP device, its hardware, software control, peripheral devices of the NAP device system used in the data capture and the sensors used on the user of the device. [16] is the NAP software on any handheld device; [18] is the tablet or phone; and [20] are the Bluetooth hardware and communication protocol.

Figure 5:
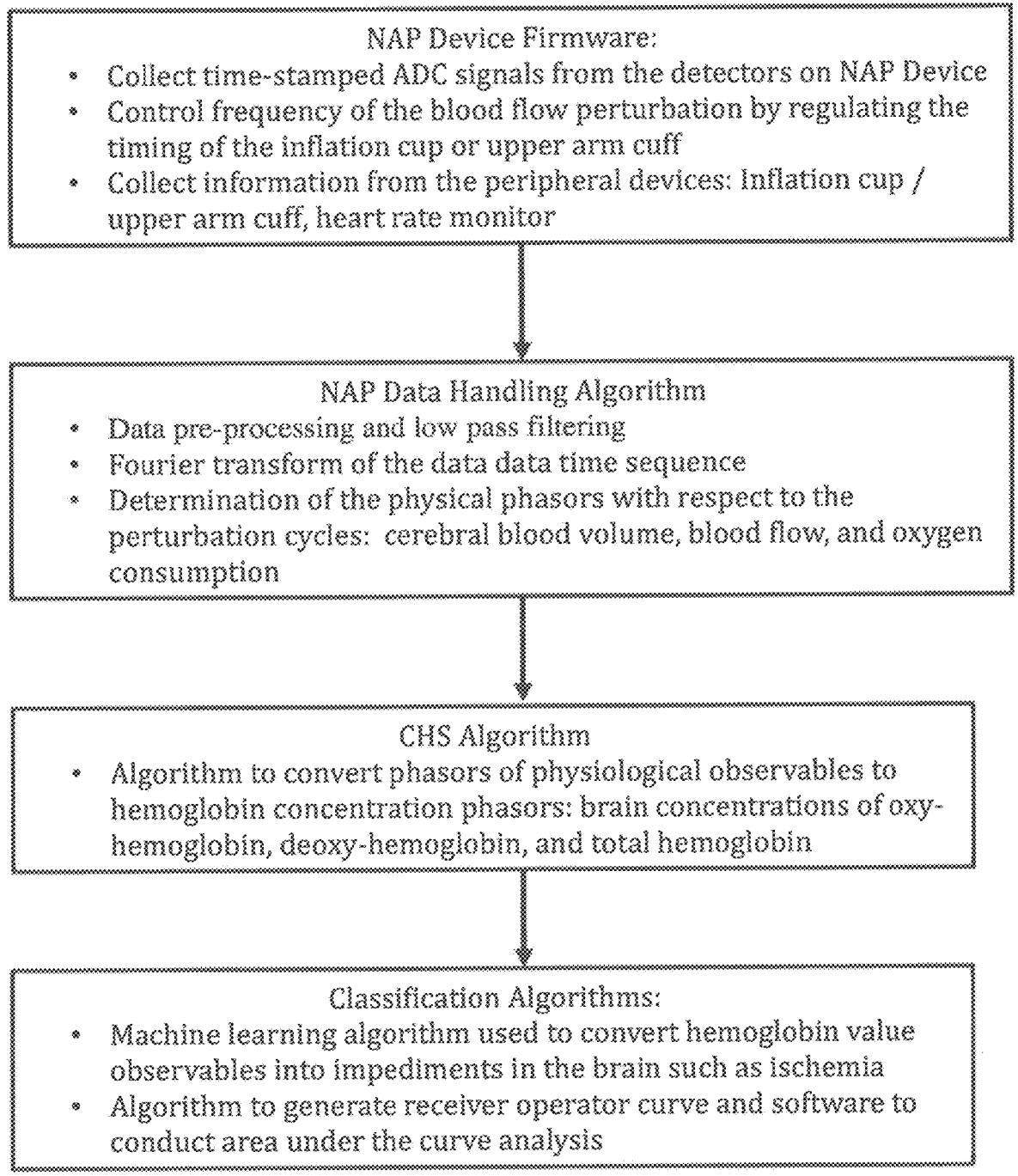
FIG. 5 illustrates a process to fire the light sources at different wavelength to collect detector data simultaneously with the phase of compression cuff expansion or contraction.

A software control data-handling algorithm as shown in FIG. 5 is used to process and correct the raw data acquired by the data acquisition electronics. FIG. 5 is the flow chart of the entire NAP system on how it is used with other standard algorithms to determine ischemic events or other impediments in the brain.

An enabling technology is the IR source-detector pairing. The measurement precision required by the algorithm determines the hardware specifications of the device. A representative specification for the source-detector is shown in the following:

| Requirement | Threshold |
| --- | --- |
| Number of source-detector pairs: | at least 8 |
| Source mode: | Continuous Wave (CW) |
| Source wavelengths: | 690 and 830 nm |
| Source power: | 0.18 W/cm2 |
| Detector dynamic range: | 12 bits |
| Sampling Frequency: | 2-10 Hz (variable) |
| Signal-to-Noise: | 1000 to 1 |
| Acquisition time: | 10 min |
| Total power: | 10 Watt |

The device will take advantage of a modified Beer-Lambert law by measuring amplitude decay of continuous wave (CW) IR incident light. Light intensity changes collected at the detector location will be translated in chromophore concentration changes, namely deoxy- and oxy-hemoglobin concentration changes. The probing IR light may be provided by a coherent laser source at two wavelengths that enables the measurement of the deoxy- and oxy-hemoglobin concentration changes in the probed brain areas.

The power range of the laser sources will be within the safe limit. A source embodiment may be configured with a single IR laser with a fiber beam splitter, which will feed all sources through a plurality of fiber optic cables.

Figure 6:
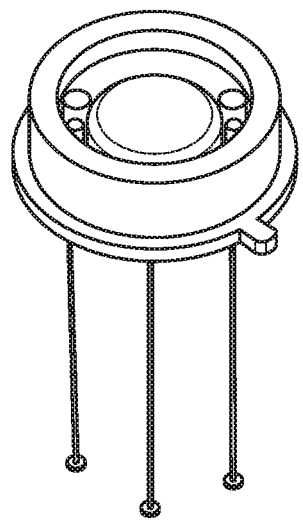
FIG. 6 shows standard silicon avalanche photo-diode (APD).

The photo detector may be based on an avalanche photodiode (APD) technology. FIG. 6 shows standard silicon APD manufactured and sold by Hamamatsu Inc. Performance specifications for this low cost device include: a spectral sensitivity range of 400 to 1000 nm, with a peak sensitivity at 800 nm, which is ideal for our application. In addition, it has a sensitivity and low noise, while operating at relatively low break down voltage, ~150 V.

FIG. 3 shows the block diagram of the hardware solution, the APD signal is digitized in a high speed ADC. A data acquisition system will be used to control the device and sample the ADC data in a multiplexed fashion with sampling rate of 0.1-10 Hz. The acquired data may be transmitted to a computing device configured as a data analysis device, such as a PC, a tablet or a smartphone. The computing device can include a fast CPU to analyze collected data and fit a mathematical model to isolate clinically relevant parameters.

The device may be powered with a power source, such as a standard Li-ion battery, preferably with at least 4 hours of continuous operation capacity on a single charge.

The device can be manufactured by using specialized material like ceramic, plastics, or carbon fiber for the spokes. The hub can include data acquisition electronics made up of layers of Kapton® or FR-4 (grade designation for industry standard composite material of certain type) and Ball Grid Arrays (BGAs) and other electronic components. The source is powered through a laser device and the detectors could be manufactured using silicon photo diode material. The device is configured and adapted to fit the footprint of a human head.

Figure 4:
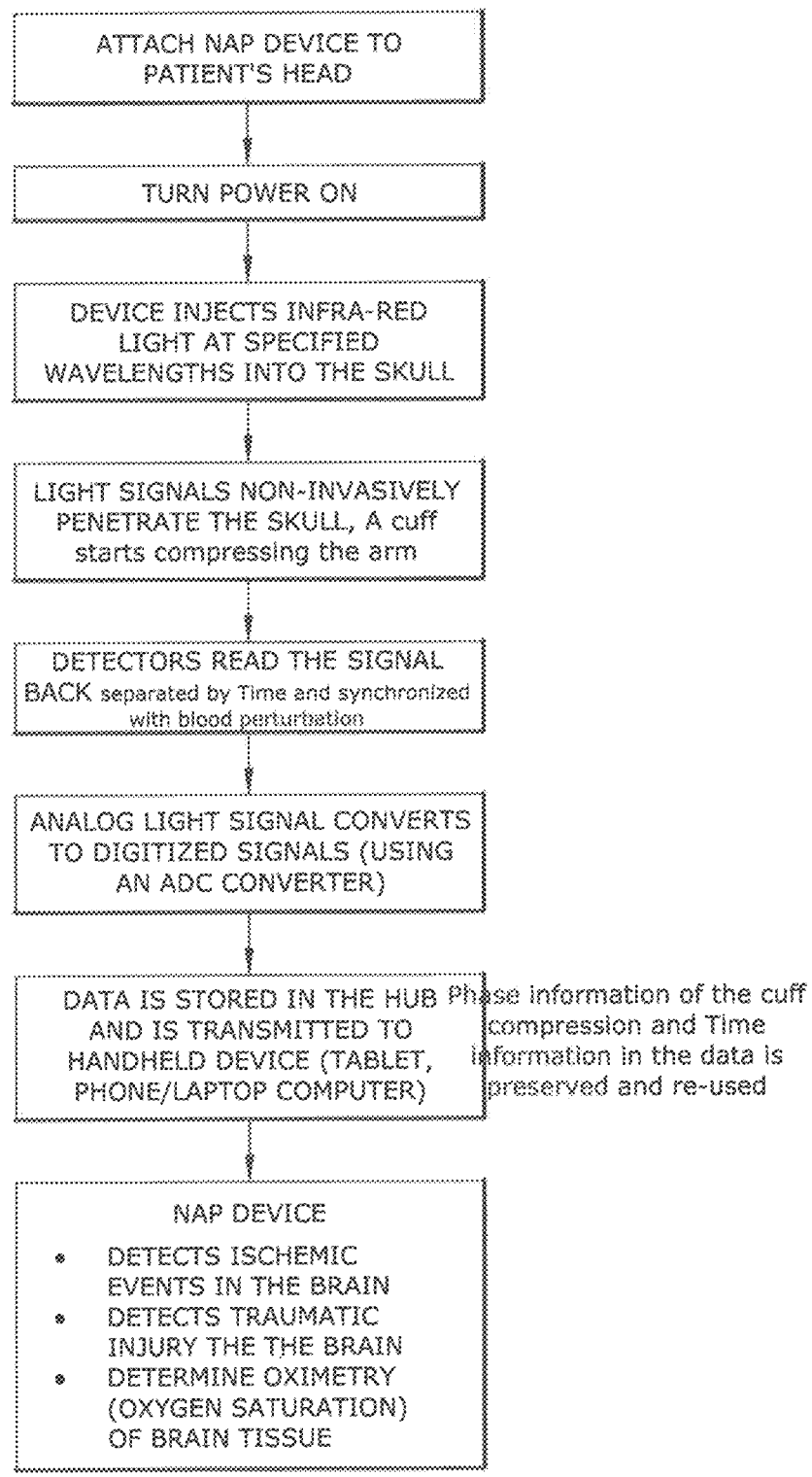
FIG. 4 illustrates a dynamic information gathering process.

Most background art measures changes in concentration of oxygenated and de-oxygenated hemoglobin in blood using Near Infra Red Spectroscopic signal and from static information of data i.e. there is no time variant information present in the data. As shown in FIG. 4, NAP device applies a dynamic information gathering process; first the systems use the same detector to capture the light emitted by the sources at the two varying wavelengths, separated by time. Additionally, it uses an external device or cuff attached to the body to induce time varying perturbations to the blood flow in the brain. FIG. 4 is the flow chart of the invention and the NAP device functional flow and data acquisition diagram.

As shown in FIG. 5, NAP device also uses a software control to fire the light sources at different wavelength to collect detector data simultaneously with the phase of compression cuff expansion or contraction. These combination of data flow as shown in FIG. 4 and FIG. 5 allows for temporal information or resolution to be stored and later reused as an input into commercially available software algorithms that can then derive additional modality.

Additionally, NAP device by acquiring time variant signal and by performing software processing such as low pass filter and Fourier transformation that converts the signal to frequency domain that can then be used by published algorithms such as Coherent hemodynamic spectroscopy (WO2014099124 A1) to facilitate acquisition of multi-modality system benefits using simple single modality instrumentation. This unique value proposition makes this device an ideal diagnostic and predictive tool for ischemic stroke and in particular TIA.

In one embodiment, NAP device signal output signal can also be used as input signal for neural networks and deep learning algorithms. This allows the system to move from the diagnostic instrumentation space to predictive analytics instrumentation phase. With sufficient data training, the device output can help to predict the occurrence of a stroke.

In one embodiment a multi-distance time variant signal information using plurality of sources on the same probe can be fired synchronously or asynchronously (e.g., all eight detectors can get data at time t0 or half at t0 and half at time t+1).

The flexible FR4 or Kapton® based hinge [13] (emanating from middle of spoke [12]) supports the plurality of sources that can be placed on either side (left and right) of the said detector [14]. In this case the source-detector-source coupling can be formed that can simultaneously fire both wavelengths of light probe. Because each wavelength will traverse a different length through the tissue, the same detector can capture both the signals with a time delay.

Flexible spoke or probe has multiple sources along the radial length of the probe [12] with a single detector. Similar to above, two wavelengths of laser light can be used simultaneously and captured with a time lag in the same detector.

Various configurations and embodiments may be employed. The hub for example can be positioned at the top of the head or centralized location or to either side of the head. The spokes could be made of elastic. The spokes could be fit in a different position compared to the position depicted in the figures.

The NAP device will be worn by the patient on his/her head, and is operably powered on by a switch and will preferably run on battery power. The device will use its laser source to inject infra-red light at specified wavelengths (at least two) into the skull at different position as determined by the location of the spokes. These light signals will non-invasively penetrate the skull to a depth of approximately 2.5 cm and will form a banana shape, moving through the tissue. The light signals will exit out at a different location where the detector placed in the spoke will read the signal back. The analog light signal will be converted into a digitized signal using an ADC converter. The data will be stored in the memory module in the hub and it will be transmitted to a handheld device (tablet/phone/laptop computer) either using a wireless protocol or using a Bluetooth protocol.

In some embodiments, a device according to the present invention can be used for early detection of transient ischemic attack, which the medical community considers as a precursor or warning indicator for an impending and disabling ischemic stroke and to detect ischemic events in the brain, to detect traumatic injury to the brain, or to determine oximetry (oxygen saturation) of brain tissue or to detect early onset of Alzheimer disease.

The NAP may be augmented with one or more peripheral patient monitoring devices, such as a blood pressure monitor, heart rate monitor, temperature, and the like. The peripheral devices may also be configured for wireless communication with the NAP and relayed to the computing device.

The system of the present invention may include at least one computer with a user interface. The computer may include any computer including, but not limited to, a desktop, laptop, and smart device, such as, a tablet and smart phone. The computer includes a program product including a machine-readable program code for causing, when executed, the computer to perform steps. The program product may include software which may either be loaded onto the computer or accessed by the computer. The loaded software may include an application on a smart device. The software may be accessed by the computer using a web browser or an application (such as an Apple iOs® based application or a Google Android® based application) if used on a smart device. The computer may access the software via the web browser using the internet, extranet, intranet, host server, internet cloud and the like.

The computer-based data processing system and method described above is for purposes of example only, and may be implemented in any type of computer system or programming or processing environment, or in a computer program, alone or in conjunction with hardware. The present invention may also be implemented in software stored on a computer-readable medium and executed as a computer program on a general purpose or special purpose computer. For clarity, only those aspects of the system germane to the invention are described, and product details well known in the art are omitted. For the same reason, the computer hardware is not described in further detail. It should thus be understood that the invention is not limited to any specific computer language, program, or computer. It is further contemplated that the present invention may be run on a stand-alone computer system, or may be run from a server computer system that can be accessed by a plurality of client computer systems interconnected over an intranet network, or that is accessible to clients over the Internet. In addition, many embodiments of the present invention have application to a wide range of industries. To the extent the present application discloses a system, the method implemented by that system, as well as software stored on a computer-readable medium and executed as a computer program to perform the method on a general purpose or special purpose computer, are within the scope of the present invention. Further, to the extent the present application discloses a method, a system of apparatuses configured to implement the method are within the scope of the present invention.

Although the subject matter has been described in terms of certain embodiments, other embodiments, including embodiments which may or may not provide various features and advantages set forth herein will be apparent to those of ordinary skill in the art in view of the foregoing disclosure. The specific embodiments described above are disclosed as examples only, and the scope of the patented subject matter is defined by the claims that follow.

The invention claimed is:

1. A neuro attack monitoring device comprising:
a hub configured for positioning on a subject's head, said hub housing at least one of data acquisition electronics, communication hardware, and software protocols;
a plurality of spokes radially extending from the hub; each of said spokes comprising at least one light source and at least one detector, at least one of said spokes comprising a hinge supporting at least two extensions, wherein at least one of the extensions is swivable relative to the other, and wherein on one of the extensions at least one light source is disposed and on the other extension at least one detector is disposed, wherein each of said spokes is configured for positioning on the subject's head such that radiation emitted by at least one light source associated with that spoke targets a region of the subject's brain; and
software control for activating the light sources associated with the plurality of spokes to emit light that is modulated between two different wavelengths over time, wherein the data acquisition electronics are configured to: for each of the plurality of light detectors, capture and collect signal data generated by that detector, and wherein said software control, processes said collected signal data to determine occurrence of an ischemic event.

2. The system of claim 1, further comprising a device configured for coupling to a portion of the subject's body for causing time-varying perturbations to the subject's blood flow.

3. The system of claim 2, wherein said device comprises a compression cuff.

4. The system of claim 3, wherein said data acquisition electronics are configured to collect said signal data synchronously with phase of contraction and expansion of said compression cuff.

5. The system of claim 1, wherein each of said light sources emit infrared radiation.

6. The system of claim 5, wherein said light sources emit continuous-wave radiation.

7. The system of claim 1, wherein one of said wavelengths is 690 nm and other wavelength is 830 nm.

8. The system of claim 1, wherein said software control is configured to activate sequentially said light sources associated with said spokes.

9. The system of claim 1, wherein said software control processes said signal data to determine time variations of oxy- and deoxy- hemoglobin levels in said target regions of the subject's brain.

10. The system of claim 9, wherein said software control converts said time variations from time domain data to frequency domain data.

11. The system of claim 10, wherein said software control employs said frequency domain data in coherent hemodynamic spectroscopy analysis method to determine occurrence of said ischemic event.

12. The system of claim 1, wherein said at least one light source comprises a plurality of light sources and said software control is configured to activate each of said light sources such that each light source emits radiation concurrently at said two wavelengths.

13. The system of claim 1, wherein each of said spokes comprises two light sources generating light of different wavelengths and at least one photodiode detector.

14. The system of claim 1, wherein said software control modulates the light between said two wavelengths at a rate greater than 3 Hz.

* * * * *